(12) United States Patent
Burkholz et al.

(10) Patent No.: US 12,310,729 B2
(45) Date of Patent: May 27, 2025

(54) BLOOD COLLECTION SYSTEM WITH AUTOMATIC PRESSURE MANAGEMENT AND RELATED METHODS

(71) Applicant: Becton, Dickinson and Company, Franklin Lakes, NJ (US)

(72) Inventors: Jonathan Karl Burkholz, Salt Lake City, UT (US); Megan Scherich, Salt Lake City, UT (US); Curtis H. Blanchard, Riverton, UT (US); Bin Wang, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 82 days.

(21) Appl. No.: 17/086,982

(22) Filed: Nov. 2, 2020

(65) Prior Publication Data
US 2021/0137436 A1 May 13, 2021

Related U.S. Application Data

(60) Provisional application No. 62/934,960, filed on Nov. 13, 2019.

(51) Int. Cl.
*A61B 5/15* (2006.01)
(52) U.S. Cl.
CPC .. *A61B 5/150389* (2013.01); *A61B 5/150221* (2013.01); *A61B 5/150992* (2013.01)
(58) Field of Classification Search
CPC ........ A61B 5/150389; A61B 5/150221; A61B 5/150992; A61B 5/150946; A61B 5/1545; A61B 5/150503; A61B 5/150572; A61B 5/15003; A61B 5/154; A61B 5/1438; A61M 25/0026; A61M 25/0043; A61M 25/0075; A61M 25/0084; A61M 25/0097; A61M 2025/0035; A61M 2210/12
See application file for complete search history.

(56) References Cited

U.S. PATENT DOCUMENTS

| | | | |
|---|---|---|---|
| 4,207,870 A | 6/1980 | Eldridge | |
| 4,212,308 A * | 7/1980 | Percarpio | A61B 5/150053 600/577 |
| 4,409,991 A | 10/1983 | Eldridge | |
| 4,583,968 A * | 4/1986 | Mahurkar | A61M 5/1582 604/523 |
| 5,281,199 A | 1/1994 | Ensminger et al. | |

(Continued)

FOREIGN PATENT DOCUMENTS

| | | |
|---|---|---|
| CN | 102698350 A | 10/2012 |
| CN | 214387460 U | 10/2021 |

(Continued)

*Primary Examiner* — Michael R Bloch
*Assistant Examiner* — Nidhi N Patel
(74) *Attorney, Agent, or Firm* — The Webb Law Firm

(57) ABSTRACT

A blood collection system may include a needle assembly, which may include a needle configured to receive an evacuated blood collection tube. The blood collection system may include a tubing, which may include a distal end and a proximal end. The proximal end may be coupled to the needle assembly. The tubing may include a first flow channel and a second flow channel. The first flow channel may be configured to collapse at a lower pressure differential than the second flow channel.

7 Claims, 18 Drawing Sheets

(56) References Cited

U.S. PATENT DOCUMENTS

| | | | |
|---|---|---|---|
| 5,807,311 A * | 9/1998 | Palestrant | A61M 25/003 604/537 |
| 5,868,717 A | 2/1999 | Prosl | |
| 6,641,555 B1 | 11/2003 | Botich et al. | |
| 7,806,869 B2 | 10/2010 | Nilsson et al. | |
| 10,391,275 B2 | 8/2019 | Burnett et al. | |
| 11,439,791 B2 | 9/2022 | Ishida | |
| 2010/0114017 A1 * | 5/2010 | Lenker | A61B 17/221 606/200 |
| 2012/0157924 A1 * | 6/2012 | Schutz | A61M 39/26 604/175 |
| 2016/0030708 A1 | 2/2016 | Casiello et al. | |
| 2016/0089071 A1 * | 3/2016 | Crawford | A61B 5/150732 600/579 |
| 2018/0140240 A1 | 5/2018 | Bullington et al. | |
| 2020/0121896 A1 * | 4/2020 | Baid | A61M 25/0606 |
| 2021/0137436 A1 | 5/2021 | Burkholz et al. | |

FOREIGN PATENT DOCUMENTS

| | | |
|---|---|---|
| JP | H11507862 | 7/1999 |
| JP | 2001522626 A | 11/2001 |
| JP | 201843028 A | 3/2018 |
| JP | 2018538116 A | 12/2018 |
| WO | 2018174251 A1 | 9/2018 |
| WO | 2018181196 A1 | 10/2018 |

* cited by examiner

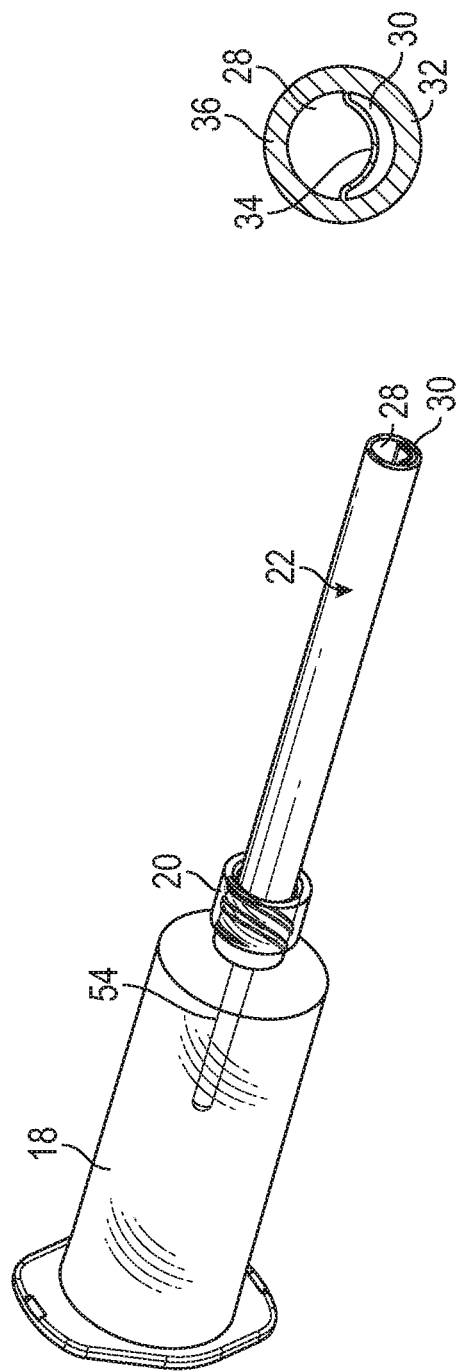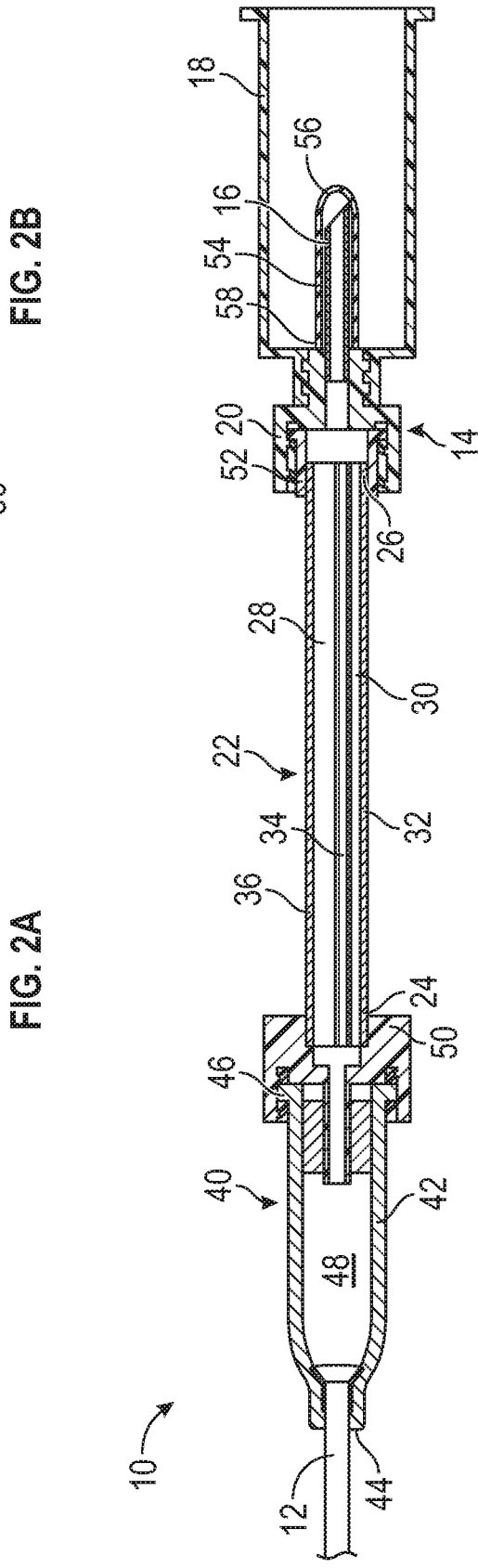

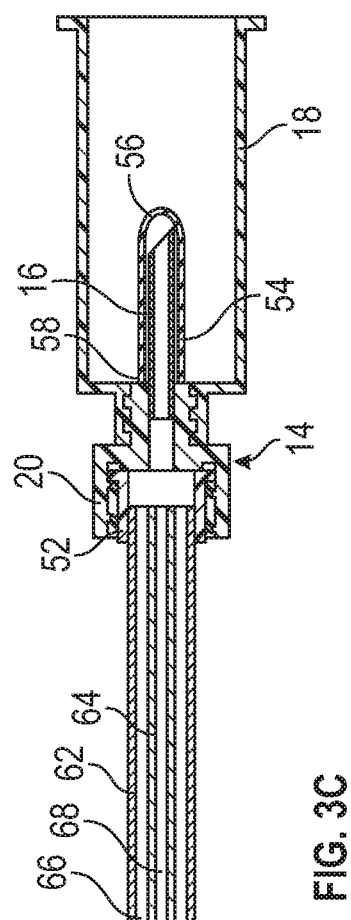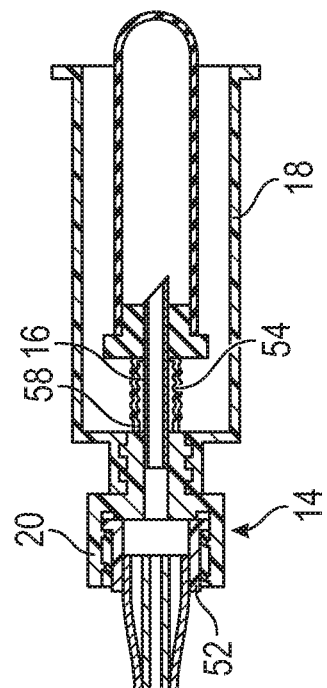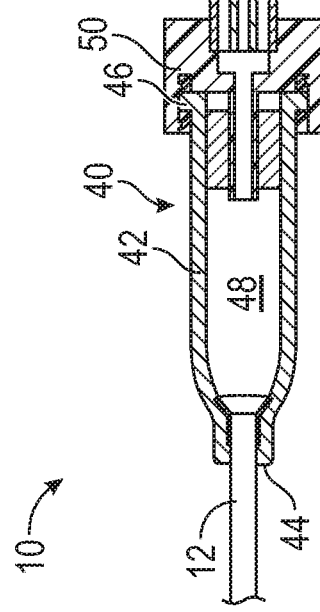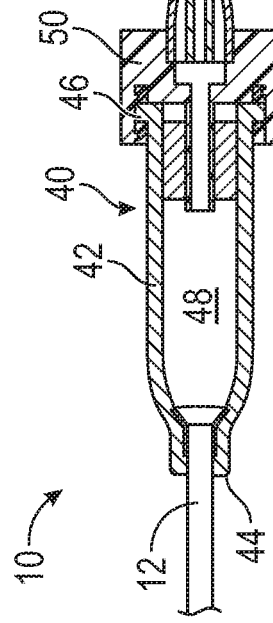
FIG. 3C
FIG. 3D

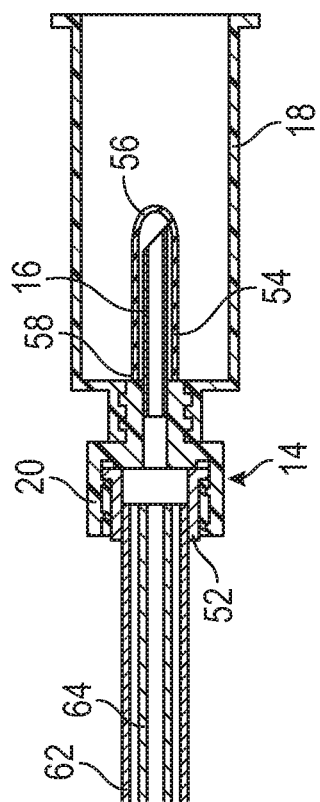
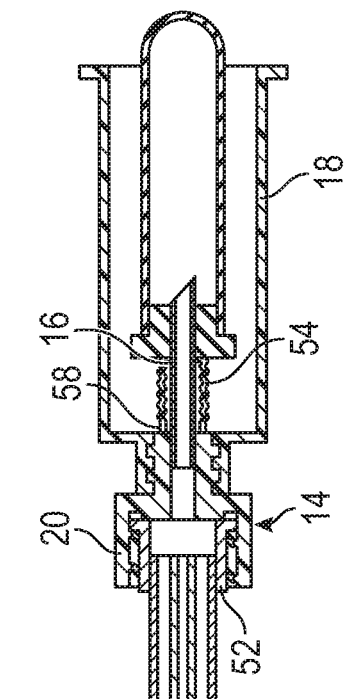
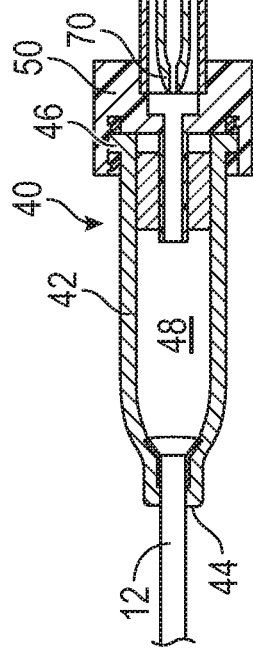
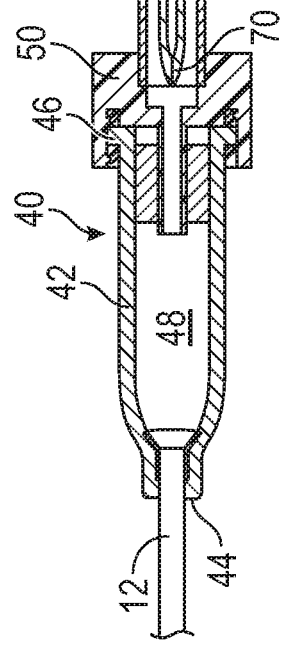
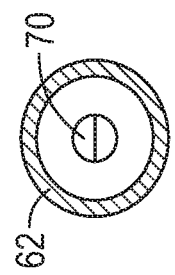
FIG. 12A
FIG. 12B
FIG. 12C
FIG. 12D

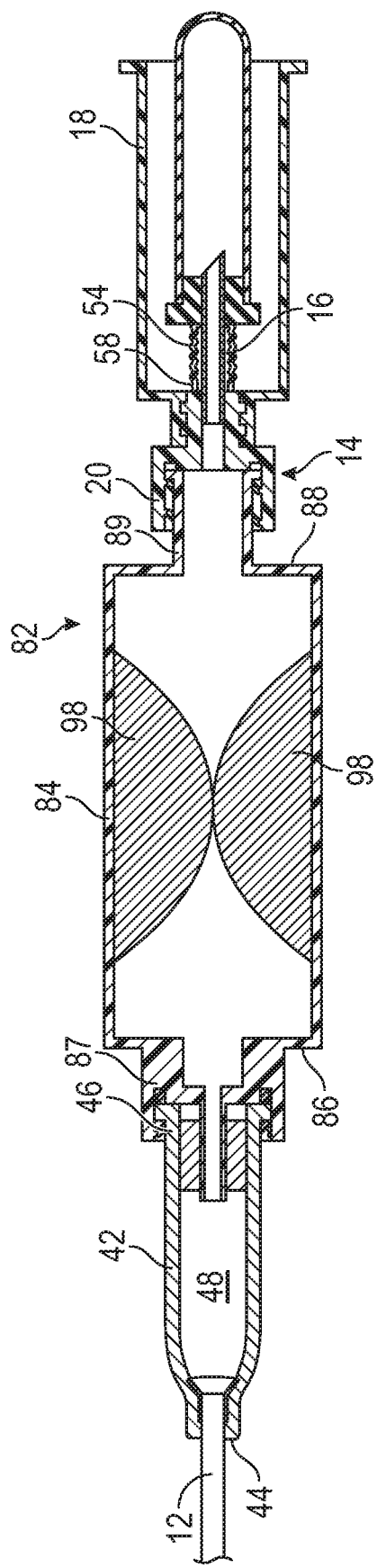
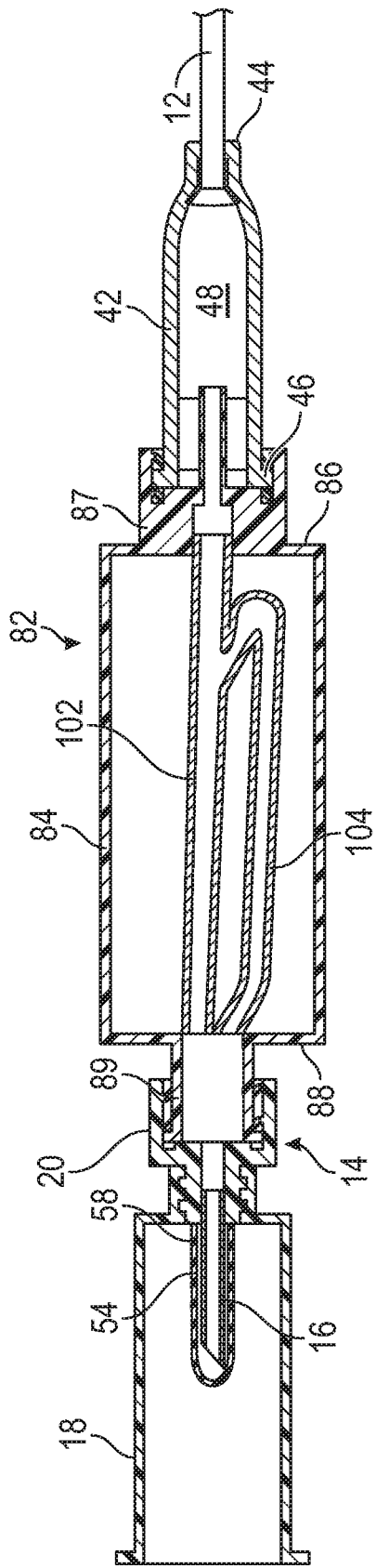
FIG. 16B
FIG. 17

BLOOD COLLECTION SYSTEM WITH AUTOMATIC PRESSURE MANAGEMENT AND RELATED METHODS

RELATED APPLICATIONS

This application claims the benefit of U.S. Provisional Application No. 62/934,960, filed Nov. 13, 2019, and entitled BLOOD COLLECTION SYSTEM WITH AUTOMATIC PRESSURE MANAGEMENT AND RELATED METHODS, which is incorporated herein in its entirety.

BACKGROUND

Intravenous catheters are commonly used for a variety of infusion therapies. For example, intravenous catheters may be used for infusing fluids, such as normal saline solution, various medicaments, and total parenteral nutrition, into a patient. Intravenous catheters may also be used for withdrawing blood from the patient.

Common types of intravenous catheter are peripheral IV catheters ("PIVCs"), peripherally inserted central catheters ("PICCs"), and midline catheters. Intravenous catheters may include "over-the needle" catheters, which may be mounted over a needle having a sharp distal tip. The sharp distal tip may be used to pierce skin and the vasculature of the patient. Insertion of the intravenous catheter into the vasculature may follow the piercing of the vasculature by the needle. The needle and the intravenous catheter are generally inserted at a shallow angle through the skin into the vasculature of the patient with a bevel of the needle facing up and away from the skin of the patient.

In order to verify proper placement of the introducer needle and/or the intravenous catheter in the vasculature, a user generally confirms that there is flashback of blood, which may be visible to the user. In some instances, the introducer needle may include a notch disposed towards a distal end of the introducer needle, and in response to the distal tip of the introducer needle being positioned within the vasculature, blood may flow proximally through a needle lumen, exit the needle lumen through the notch, and then travel proximally between an outer surface of the introducer needle and an inner surface of the intravenous catheter.

Accordingly, where the intravenous catheter is at least partially transparent, the user may visualize a small amount of blood "flashback" and thereby confirm placement of the intravenous catheter within the vasculature. Presence of a vasculature entrance indicator, such as flashback, may facilitate successful placement of intravenous catheters. Once placement of the introducer needle within the vasculature has been confirmed, the user may temporarily occlude flow in the vasculature and withdraw the introducer needle, leaving the intravenous catheter in place for future blood withdrawal and/or fluid infusion.

For blood withdrawal, an evacuated blood collection tube may be used. An evacuated blood collection tube includes a test tube with a rubber stopper at one end. The evacuated blood collection tube has had all or a portion of air removed from the test tube so pressure within the evacuated blood collection tube is lower than ambient pressure. Such an evacuated blood collection tube is often referred to as an internal vacuum or a vacuum tube. A commonly used evacuated blood collection tube is a VACUTAINER® blood collection tube, available from Becton, Dickinson & Company.

To collect a blood sample from a patient, an adapter is coupled to the needle or the intravenous catheter. The adapter includes an additional needle that penetrates the rubber stopper of the evacuated blood collection tube. When the rubber stopper is penetrated, a pressure in the vein is higher than a pressure in the evacuated blood collection tube, which pushes blood into the evacuated blood collection tube, thus filling the evacuated blood collection tube with blood. A vacuum within the evacuated blood collection tube decreases as the evacuated blood collection tube fills, until the pressure in the evacuated blood collection tube equalizes with the pressure in the vein, and the flow of blood stops.

Unfortunately, as blood is drawn into the evacuated blood collection tube, red blood cells are in a high shear stress state and susceptible to hemolysis due to a high initial pressure differential between the vein and the evacuated blood collection tube. Hemolysis may result in rejection and discard of a blood sample. The high initial pressure differential can also result in catheter tip collapse, vein collapse, or other complications that prevent or restrict blood from filling the evacuated blood collection tube.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to a blood collection system with automatic pressure management, as well as related devices and methods. In some embodiments, a blood collection system may provide a fluid pathway between a catheter and an evacuated blood collection tube that has an inner diameter that is responsive to a pressure differential between the evacuated blood collection tube and a vein of a patient. In some embodiments, in response to coupling of the evacuated blood collection tube to the blood collection system, a spike in the pressure differential may occur. In some embodiments, in response to the spike in the pressure differential, an inner diameter of a portion of the fluid pathway may decrease, which may increase a fluidic resistance of the fluid pathway and slow blood flow into the blood collection system. In some embodiments, the decreased blood flow may reduce a risk of hemolysis. In some embodiments, the decreased blood flow may also reduce a risk of collapse of the vein and/or the catheter.

In some embodiments, as the evacuated blood collection tube fills with blood, a vacuum within the evacuated blood collection tube may decrease, and the pressure differential between the evacuated blood collection tube and the vein may decrease. In some embodiments, the decreased pressure differential may result in the inner diameter of the portion of the fluid pathway increasing, which may reduce the fluidic resistance and increase a flow rate of blood into the blood collection system. Thus, despite the decrease in the pressure differential, the evacuated blood collection tube may still fill quickly.

In some embodiments, the blood collection system may include a needle assembly, which may include a needle configured to receive the evacuated blood collection tube. In some embodiments, the blood collection device may include a blood collection tube holder, which may be coupled to the needle assembly and surround the needle. In some embodiments, the blood collection system may include a tubing, which may include a distal end and a proximal end. In some embodiments, the proximal end may be coupled to the needle assembly. In some embodiments, the tubing may include a first flow channel and a second flow channel. In some embodiments, the fluid pathway of the blood collection system may include the first flow channel and the second flow channel.

In some embodiments, the first flow channel may be configured to collapse at a lower pressure differential than the second flow channel. In some embodiments, the first flow channel may collapse in response to the spike in the pressure differential between the evacuated blood collection tube and a vein of a patient. In some embodiments, the second flow channel may not collapse in response to the spike in the pressure differential. In some embodiments, because the second flow channel remains open but the first flow channel collapses, the inner diameter may decrease but the fluid pathway may remain open. In some embodiments, as the evacuated blood collection tube fills with blood, the first flow channel may open, allowing a flow rate of blood to increase.

In some embodiments, a fluidic resistance of the first flow channel may be less than a fluidic resistance of the second flow channel. In these embodiments, the fluidic resistance of the first flow channel may be less than the fluidic resistance of the second flow channel because a size or diameter of the first flow channel may be greater than a size or diameter of the second flow channel. In some embodiments, the first flow channel may be formed by a first wall and a shared wall, which may be shared between the first flow channel and the second flow channel. In some embodiments, the second flow channel may be formed by a second wall and the shared wall. In some embodiments, the first wall may include a lower durometer than the second wall. In some embodiments, the second flow channel may include a bore hole. In some embodiments, the bore hole may extend from the distal end of the tubing to the proximal end of the tubing.

In some embodiments, the blood collection system may include a catheter assembly. In some embodiments, the catheter assembly may include a catheter adapter, which may include a distal end, a proximal end, and a lumen extending through the distal end of the catheter adapter and the proximal end of the catheter adapter. In some embodiments, the distal end of the tubing may be coupled to the catheter adapter. In some embodiments, the catheter assembly may include the catheter extending distally from the distal end of the catheter adapter. In some embodiments, the blood collection system may include a male luer adapter coupled to the distal end of the tubing, and a female luer adapter coupled to the proximal end of the tubing. In some embodiments, the catheter assembly may be replaced with a needle set, which may be coupled to the distal end of the tubing.

In some embodiments, the blood collection system may include an outer tubing and an inner tubing. In some embodiments, an inner diameter of the outer tubing may be greater than an outer diameter and an inner diameter of the inner tubing. In some embodiments, the blood collection system may include another first flow channel and another second flow channel. In some embodiments, the other first flow channel may extend between the outer tubing and the inner tubing. In some embodiments, the other second flow channel may extend through the inner tubing. In some embodiments, the other first flow channel may be configured to collapse at a different pressure differential than the other second flow channel.

In some embodiments, the outer tubing may include a lower durometer than the inner tubing. In some embodiments, the other first flow channel may be configured to collapse at a lower pressure differential than the other second flow channel. In some embodiments, at the lower pressure differential, the outer tubing may contact the inner tubing to close at least a portion of the other first flow channel.

In some embodiments, the outer tubing may have a greater durometer than the inner tubing. In these and other embodiments, the other second flow channel may be configured to collapse at a lower pressure differential than the other first flow channel. In some embodiments, a distal end of the inner tubing may include a duck bill valve.

In some embodiments, the blood collection system may include another tubing, which may include no more than one flow channel. In some embodiments, an inner surface of the other tubing may include one or more ribs or one or more slots. In some embodiments, in response to the spike in the pressure differential, the slots may close, and the flow channel may remain open. In some embodiments, the slots may be configured to close when the pressure differential reaches a predetermined level. In some embodiments, the ribs may extend along a length of the other tubing and may be generally evenly spaced about a circumference of the inner surface. In some embodiments, the slots may extend outwardly from a generally cylindrical portion of the fluid channel. In some embodiments, in response to the spike in the pressure differential and the pressure differential reaching the predetermined level, the generally cylindrical portion of the fluid channel may remain open.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 2A is another cross-sectional view along the line 1B-1B of FIG. 1A, according to some embodiments;

FIG. 2B is an enlarged cross-section of another example tubing, according to some embodiments;

FIG. 2C is another cross-sectional view of the blood collection system of FIG. 1A, according to some embodiments;

FIG. 3C is another cross-sectional view of the blood collection system of FIG. 1A, according to some embodiments;

FIG. 3D is another cross-sectional view of the blood collection system of FIG. 1A, illustrating an example evacuated blood collection tube coupled to the blood collection system, according to some embodiments;

FIG. 12A is another cross-sectional view of the blood collection system of FIG. 1A, according to some embodiments;

FIG. 12B is another cross-sectional view of the blood collection system of FIG. 12A, illustrating the evacuated blood collection tube coupled to the blood collection system, according to some embodiments;

FIG. 12C is a cross-sectional view of another example tubing at a first pressure differential, according to some embodiments;

FIG. 12D is a cross-sectional view of the tubing of FIG. 12C at a second pressure differential higher than the first pressure differential, according to some embodiments;

FIG. 16B is a cross-sectional view of the blood collection system of FIG. 16A at a second pressure differential higher than the first pressure differential, according to some embodiments; and FIG. 17 is a cross-sectional view of the blood collection system of FIG. 13A, according to some embodiments.

DESCRIPTION OF EMBODIMENTS

Referring now to FIGS. 1A-1D, in some embodiments, a blood collection system 10 may provide a fluid pathway between a catheter 12 and an evacuated blood collection tube that has an inner diameter that is responsive to a pressure differential between the evacuated blood collection tube and a vein of a patient. In some embodiments, in response to coupling of the evacuated blood collection tube to the blood collection system 10, a spike in the pressure differential may occur. In some embodiments, in response to the spike in the pressure differential, an inner diameter of a portion of the fluid pathway may decrease, which may increase a fluidic resistance of the fluid pathway and slow blood flow into the blood collection system 10. In some embodiments, the decreased blood flow may reduce a risk of hemolysis. In some embodiments, the decreased blood flow may also reduce a risk of collapse of the vein and/or the catheter.

In some embodiments, the evacuated blood collection tube may be evacuated such that a pressure within the evacuated blood collection tube is lower than ambient or atmospheric pressure. In some embodiments, the evacuated blood collection tube may include any suitable evacuated blood collection tube. In some embodiments, as the evacuated blood collection tube fills with blood, a vacuum within the evacuated blood collection tube may decrease, and the pressure differential between the evacuated blood collection tube and the vein may decrease. In some embodiments, the decreased pressure differential may result in the inner diameter of the portion of the fluid pathway increasing, which may reduce the fluidic resistance and increase a flow rate of blood into the blood collection system 10. Thus, despite the decrease in the pressure differential, the evacuated blood collection tube may still fill quickly.

Figure 3A:
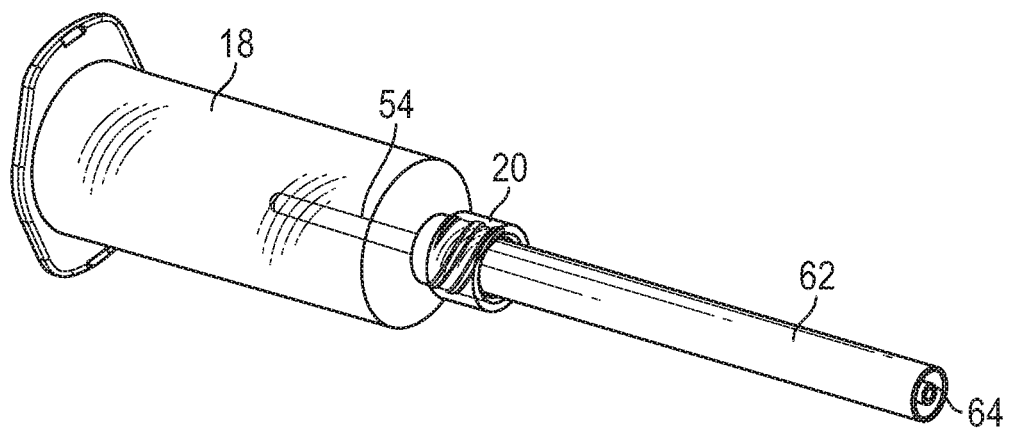
FIG. 3A is another cross-sectional view along the line 1B-1B of FIG. 1A, according to some embodiments.
Figure 3B:
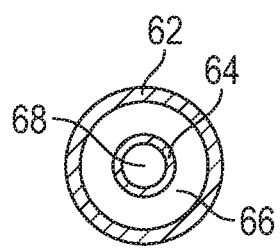
FIG. 3B is an enlarged cross-section of another example tubing, according to some embodiments.
Figure 3E:
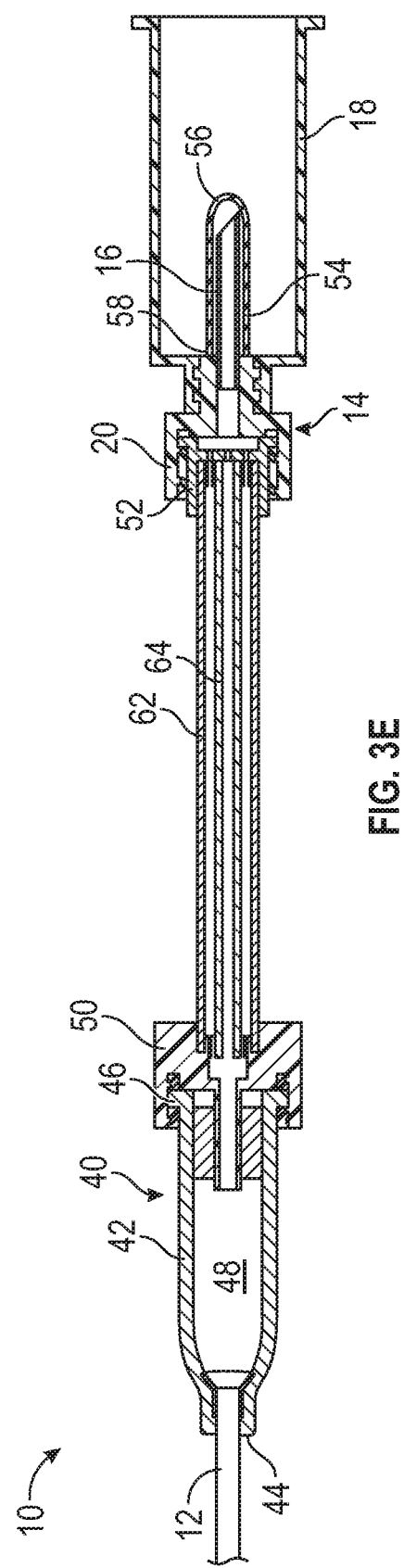
FIG. 3E is another cross-sectional view of the blood collection system of FIG. 1A, according to some embodiments.
Figure 4A:
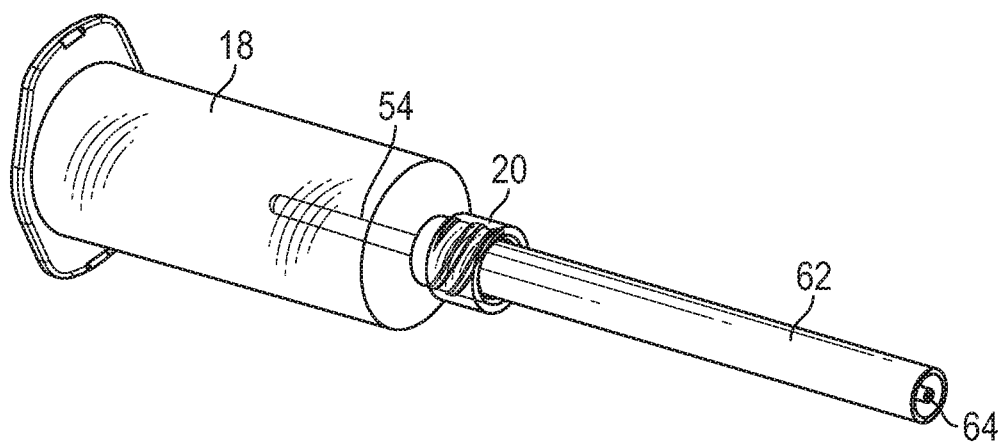
FIG. 4A is another cross-sectional view along the line 1B-1B of FIG. 1A, according to some embodiments.
Figure 4B:
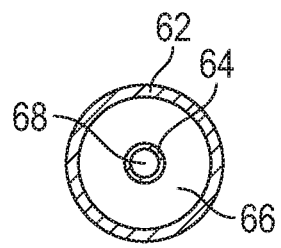
FIG. 4B is an enlarged cross-section of another example tubing, according to some embodiments.
Figure 4C:
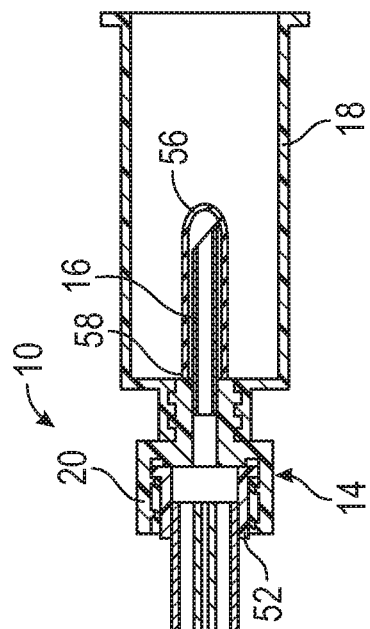
FIG. 4C is another cross-sectional view of the blood collection system of FIG. 1A, according to some embodiments.
Figure 4C:
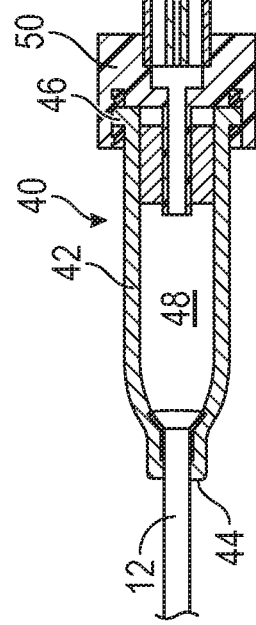
Figure 4D:
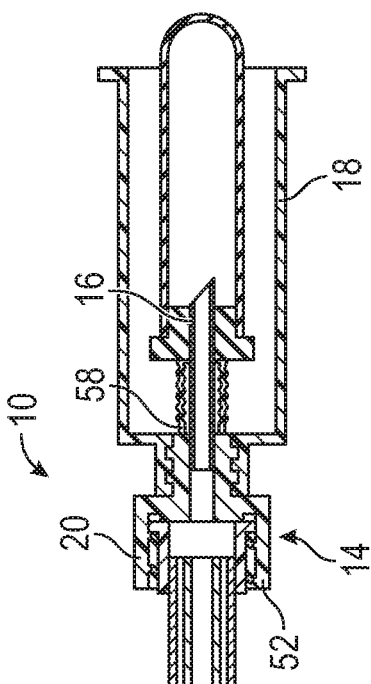
FIG. 4D is another cross-sectional view of the blood collection system of FIG. 1A, illustrating the evacuated blood collection tube coupled to the blood collection system, according to some embodiments.
Figure 4D:
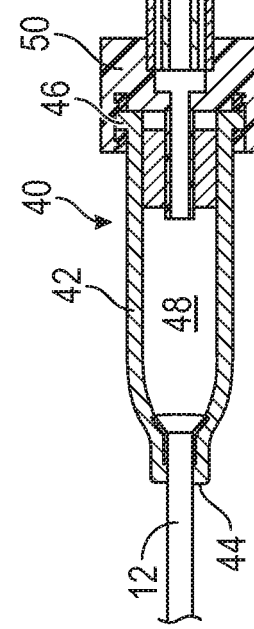

In some embodiments, the blood collection system 10 may include a needle assembly 14, which may include a needle 16 configured to receive the evacuated blood collection tube (see, e.g., FIG. 3D). In some embodiments, the needle assembly 14 may include one or more threads, which may be configured to couple to a blood collection tube holder 18, which may be generally cylindrical. In some embodiments, the blood collection tube holder 18 may surround the needle 16. In some embodiments, the needle assembly 14 may include a luer lock access device, such as, for example, the VACUTAINER® LUER-LOK™ ACCESS DEVICE available from Becton, Dickinson & Company.

In some embodiments, the needle assembly 14 may include a luer adapter 20, which may include a luer lock or luer slip connector. In some embodiments, the luer adapter 20 may include a male or female luer connector. In some embodiments, the needle 16 may extend proximally from the luer adapter 20.

In some embodiments, the blood collection system 10 may include a tubing 22, which may include a distal end 24 and a proximal end 26. In some embodiments, the proximal end 26 may be coupled to the needle assembly 14, such as, for example, the luer adapter 20 of the needle assembly 14. In some embodiments, the tubing 22 may include a first flow channel 28 and a second flow channel 30. In some embodiments, the fluid pathway of the blood collection system 10 may include the first flow channel 28 and the second flow channel 30. In some embodiments, the tubing 22 may be constructed of urethane (including polyurethanes), rubber, polyvinyl chloride (PVC), silicone, polyethylene (low density and high density), nylon, fluropolymers, polypropylene, acrylonitrile-butadiene styrene (ABS), polycarbonate, acrylic, and/or the like.

In some embodiments, the first flow channel 28 may be configured to collapse at a lower pressure differential than the second flow channel 30. In some embodiments, collapsing may include partial or complete blocking of a particular flow channel due to failing or caving in of a surrounding wall forming the particular flow channel. In some embodiments, the first flow channel 28 may collapse in response to the spike in the pressure differential between the evacuated blood collection tube and the vein of the patient. In some embodiments, when the first flow channel 28 collapses, the first flow channel may be partially or completely blocked. In some embodiments, the second flow channel 30 may not collapse in response to the spike in the pressure differential and a diameter of the second flow channel 30 may remain the same. In other embodiments, the second flow channel 30 may partially collapse in response to the spike in the pressure differential. In other embodiments, the second flow channel 30 may collapse less than the first flow channel 28 in response to the spike in the pressure differential. In some embodiments, because the second flow channel 30 remains open but the first flow channel collapses, the inner diameter of the portion of the fluid pathway may decrease but the fluid pathway may remain open. In some embodiments, as the evacuated blood collection tube fills with blood and the pressure differential decreases, the first flow channel 28 may open, allowing a flow rate of blood to increase.

In some embodiments, a fluidic resistance of the first flow channel 28 may be less than a fluidic resistance of the second flow channel. In these embodiments, the fluidic resistance of the first flow channel 28 may be less than the fluidic resistance of the second flow channel 30 because a size or diameter of the first flow channel 28 may be greater than a size or diameter of the second flow channel 30.

In some embodiments, the first flow channel 28 may be formed by a first wall 32 and a shared wall 34, which may be shared between the first flow channel 28 and the second flow channel 30. In some embodiments, the shared wall 34 may include any portion of the tubing 22 disposed between the first flow channel 28 and the second flow channel 30. In some embodiments, the second flow channel 30 may be formed by a second wall 36 and the shared wall 34. In some embodiments, the first wall 32 may include a lower durometer than the second wall 36 and/or the shared wall 34.

Figure 1A:
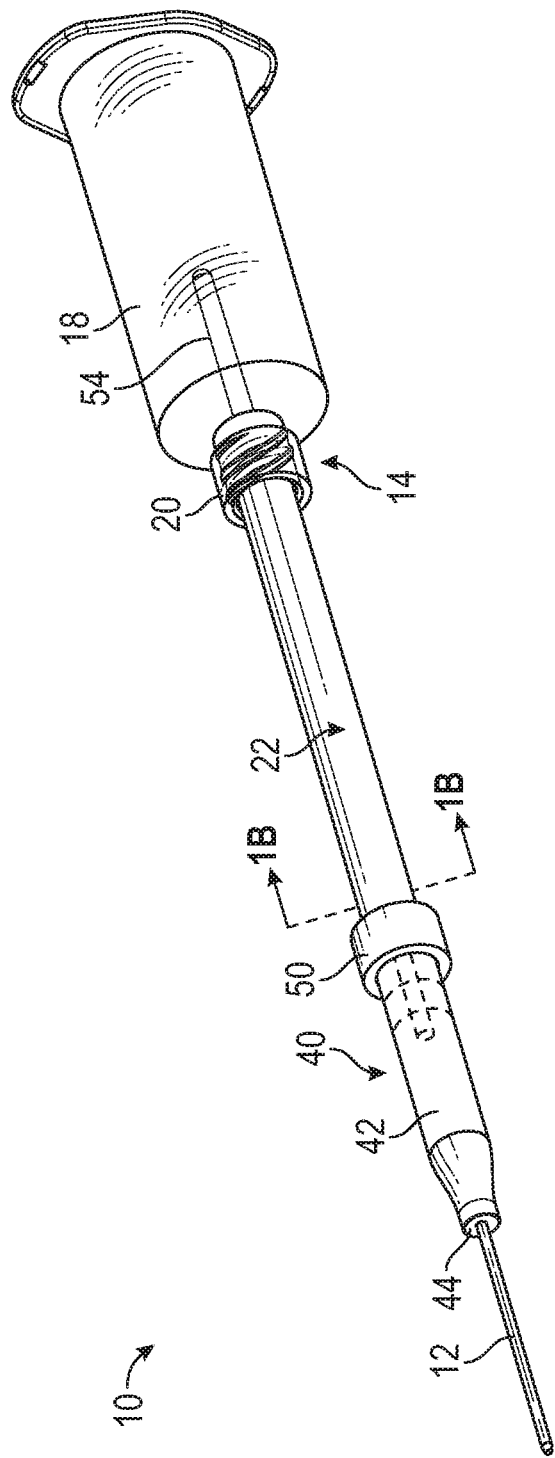
FIG. 1A is an upper perspective view of an example blood collection system, according to some embodiments.
Figure 1C:
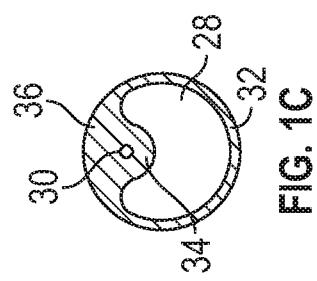
FIG. 1C is an enlarged cross-section of an example tubing, according to some embodiments.
Figure 1B:
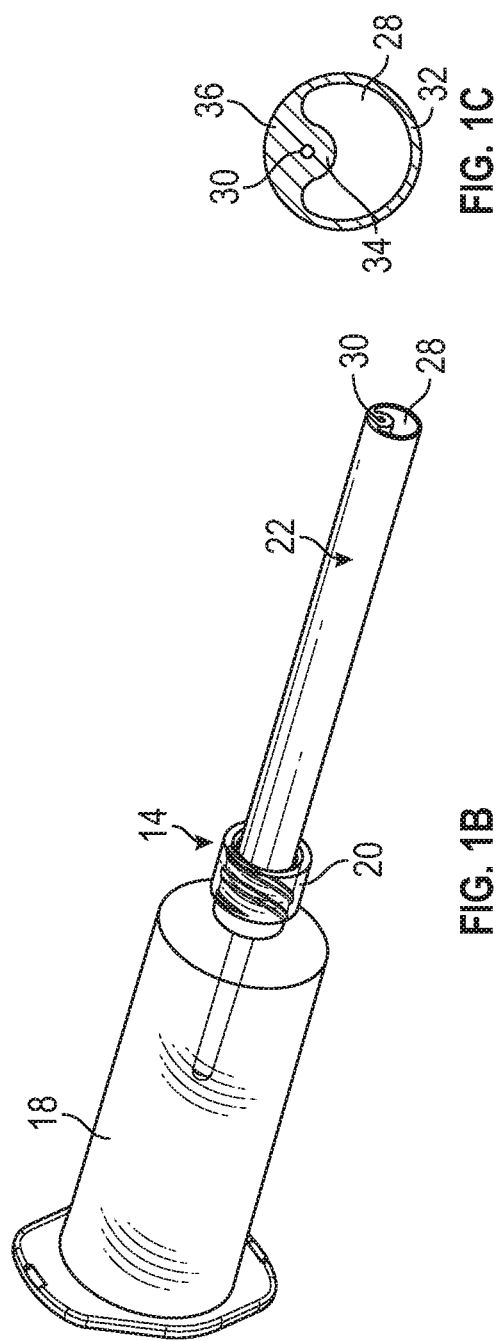
FIG. 1B is a cross-sectional view along the line 1B-1B of FIG. 1A, according to some embodiments.
Figure 1D:
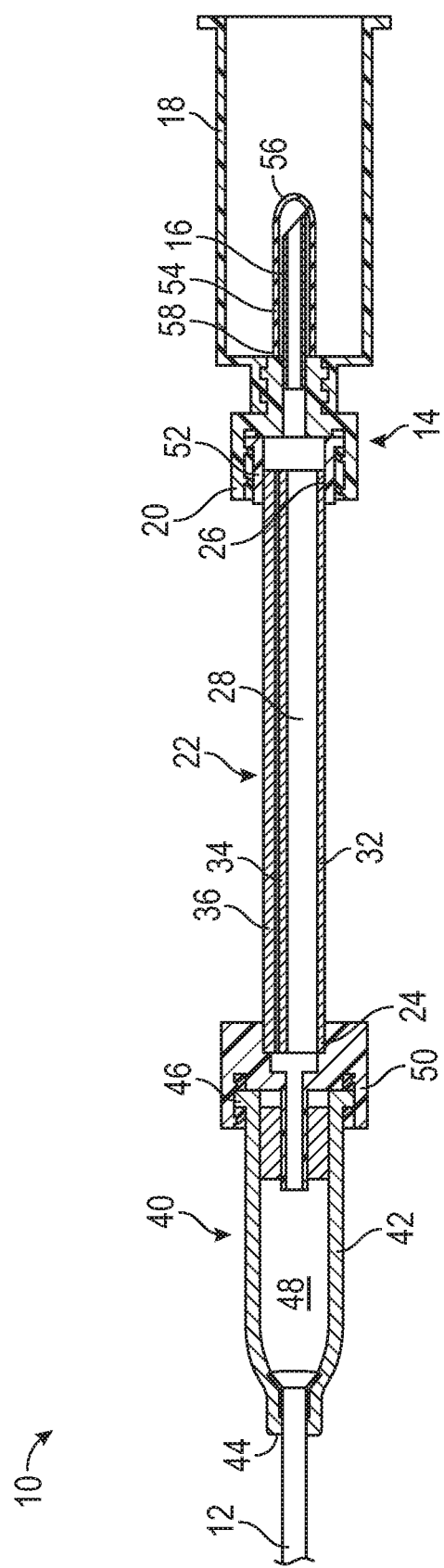
FIG. 1D is a cross-sectional view of the blood collection system of FIG. 1A, according to some embodiments.

In some embodiments, the second flow channel 30 may include a bore hole, as illustrated, for example in FIGS. 1B-1D. In some embodiments, the bore hole may extend from the distal end 24 of the tubing 22 to the proximal end 26 of the tubing 22. In some embodiments, the bore hole may extend along a majority of a length of the tubing 22 from the distal end 24 of the tubing 22 to the proximal end 26 of the tubing 22. In some embodiments, the bore hole may extend along a portion of the length of the tubing 22 from the distal end 24 of the tubing 22 to the proximal end 26 of the tubing 22. In some embodiments, the first flow channel 28 may include a shape that is generally circular with the shared wall 34 protruding inwardly towards a middle of the circle to form a general C-shape. In some embodiments, the shared wall 34 may be convex, extending towards a middle portion of the first flow channel 28.

In some embodiments, the blood collection system 10 may include a catheter assembly 40. In some embodiments, the catheter assembly 40 may include a catheter adapter 42, which may include a distal end 44, a proximal end 46, and a lumen 48 extending through the distal end 44 of the catheter adapter 42 and the proximal end 46 of the catheter adapter 42. In some embodiments, the distal end 24 of the tubing 22 may be coupled to the catheter adapter 42. In some embodiments, the catheter assembly 40 may include the catheter 12 extending distally from the distal end 44 of the catheter adapter 42. In some embodiments, the catheter assembly 40 may be replaced with a needle set, which may be coupled to the distal end 24 of the tubing 22.

In some embodiments, the blood collection system 10 may include a luer adapter 50 coupled to the distal end 24 of the tubing 22 and/or a luer adapter 52 coupled to the proximal end 26 of the tubing 22. In some embodiments, the luer adapter 50 and/or the luer adapter 52 may include a luer lock or luer slip connector. In some embodiments, the luer adapter 50 and/or the luer adapter 52 may include a male or female luer connector. In some embodiments, the proximal end 26 of the tubing 22 may be integrated with the luer adapter 20 and/or the needle assembly 14.

In some embodiments, the catheter assembly 40 may include a PIVC, such as, for example, the BD NEXIVA™ Closed IV Catheter system, the BD CATHENA™ Catheter system, the BD VENFLON™ Pro Safely Shielded IV Catheter system, the BD NEOFLON™ IV Cannula system, the BD INSYTE™ AUTOGUARD™ BC Shielded IV Catheter system, or another suitable peripheral intravenous catheter system. In some embodiments, the catheter assembly 40 may include a PICC or a midline catheter. In some embodiments, the luer adapter 50 may be coupled to the catheter adapter 42 in any number of suitable ways. For example, the luer adapter 50 may be coupled to the distal end 44 of the catheter adapter 42. As another example, the luer adapter 50 may be coupled to an extension tube extending outwardly from the catheter adapter 42.

In some embodiments, an elastomeric sheath 54 may be coupled to the needle assembly 14. In some embodiments, a proximal end of the needle 16 may be enveloped within the elastomeric sheath 54. In some embodiments, the elastomeric sheath 54 may include an open distal end 58 and a closed proximal end 56. In some embodiments, in response to the evacuated blood collection tube pushing the elastomeric sheath 54 distally, the needle 16 may pierce the elastomeric sheath 54, and the needle 16 may insert into a cavity of the evacuated blood collection tube.

Referring now to FIGS. 2A-2D, in some embodiments, a shape of the first flow channel 28 and/or the second flow channel 30 may vary. In some embodiments, the first flow channel 28 may be formed by the first wall 32 and the shared wall 34, as illustrated, for example, in FIG. 2B. In some embodiments, the second flow channel 30 may be formed by the second wall 36 and the shared wall 34, as illustrated, for example, in FIG. 2B. In some embodiments, the first wall 32 may include a lower durometer than the second wall 36 and/or the shared wall. In some embodiments, the shared wall 34 may be convex with respect to the first flow channel 28. In some embodiments, together the first flow channel 28 and the second flow channel 30 may form a generally circular shape. In some embodiments, one or more of the first wall 32, the shared wall 34, and the second wall 36 may be generally smooth.

Figure 2D:
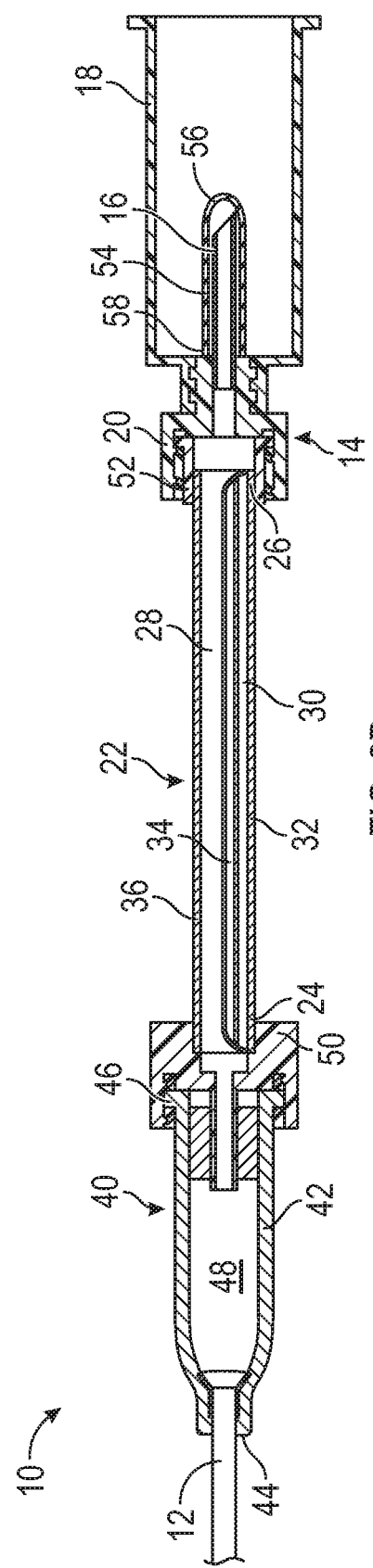
FIG. 2D is another cross-sectional view of the blood collection system of FIG. 1A, illustrating an example flow channel with closed ends, according to some embodiments.

In some embodiments, as illustrated in FIG. 2D, the second flow channel 30 may be isolated from the fluid pathway of the blood collection system 10 and may contain air, which may facilitate collapse or reduction in size of the first flow channel 28 in response to the spike in the pressure differential. In these embodiments, ends of the second flow channel 30 may be closed or sealed.

Referring now to FIGS. 3A-4D, in some embodiments, the blood collection system 10 may include an outer tubing 62 and an inner tubing 64. In some embodiments, an inner diameter of the outer tubing 62 may be greater than an inner diameter and outer diameter of the inner tubing 64. In some embodiments, the outer tubing 62 may include a first flow channel 66, and the inner tubing 64 may include a second flow channel 68. In some embodiments, the first flow channel 66 may extend between the outer tubing 62 and the inner tubing 64. In some embodiments, the second flow channel 68 may extend through the inner tubing 64, and the first flow channel 66 may extend through the outer tubing 62. In some embodiments, the first flow channel 66 and the outer tubing 62 may be configured to collapse at a different pressure differential than the second flow channel 68 and the inner tubing 64.

Referring now to FIGS. 3A-3E, in some embodiments, the outer tubing 62 may include a lower durometer than the inner tubing 64. In some embodiments, the first flow channel 66 and the outer tubing 62 may be configured to collapse at a lower pressure differential than the second flow channel 68 and the inner tubing 64. In some embodiments, at the lower pressure differential, the outer tubing 62 may contact the inner tubing 64 to close at least a portion of the first flow channel 66. In some embodiments, the first flow channel 66 and the outer tubing 62 may collapse in response to coupling the evacuated blood collection tube to the blood collection system 10, as illustrated, for example, in FIG. 3D.

In some embodiments, in response to the evacuated blood collection tube partially filling with blood, the first flow channel 66 may open. In some embodiments, the diameter of the second flow channel 68 may remain the same or substantially the same prior to and after coupling the evacuated blood collection tube to the blood collection system 10. In some embodiments, the diameter of the second flow channel 68 may remain the same prior to and after coupling the evacuated blood collection tube partially filling with blood.

In some embodiments, the inner tubing 64 may not be coupled to the outer tubing 62. In some embodiments, the inner tubing 64 may be coupled to the outer tubing 62. In some embodiments, a portion of the inner tubing 64 may be embedded in the outer tubing 62. In some embodiments, the inner tubing 64 may be secured within the outer tubing 62 by a portion of a particular adapter, as illustrated, for example, in FIG. 3E. In some embodiments, the second flow channel 68 may be isolated from the fluid pathway of the blood collection system 10 and may contain air, similar to, for example, FIG. 2D. In some embodiments, a proximal end of the inner tubing 64 and/or the outer tubing 62 may be integrated with the luer adapter 20 and/or the needle assembly 14.

Referring now to FIGS. 4A-4D, in some embodiments, the outer tubing 62 may have a greater durometer than the inner tubing 64. In some embodiments, the second flow channel 68 and the inner tubing 64 may be configured to collapse at a lower pressure differential than the first flow channel 66 and the outer tubing 62. In some embodiments, the second flow channel 68 and the inner tubing 64 may collapse in response to coupling the evacuated blood collection tube to the blood collection system 10, as illustrated, for example, in FIG. 4D. In some embodiments, in response to the evacuated blood collection tube partially filling with blood, the second flow channel 68 may open. In some embodiments, the diameter of the first flow channel 66 may remain the same prior to and after coupling the evacuated blood collection tube to the blood collection system 10. In some embodiments, the diameter of the first flow channel 66 may remain the same prior to and after coupling the evacuated blood collection tube partially filling with blood. In some embodiments, the second flow channel 68 may be isolated from the fluid pathway of the blood collection system 10 and may contain air, similar to, for example, FIG. 2D.

Referring now to FIGS. 12A-12B, in some embodiments, a distal end of the inner tubing 64 may include a duck bill valve 70. In these and other embodiments, the outer tubing 62 may have a greater durometer than the inner tubing 64. In some embodiments, the second flow channel 68 and the inner tubing 64 may collapse in response to coupling the evacuated blood collection tube to the blood collection system 10, as illustrated, for example, in FIGS. 12B and 12D. In some embodiments, in response to the second flow channel 68 and the inner tubing collapsing, the duck bill valve 70 may close. In some embodiments, in response to the evacuated blood collection tube partially filling with blood, the duck bill valve 70 and the second flow channel 68 may open, as illustrated, for example in FIG. 12C.

Figure 5A:
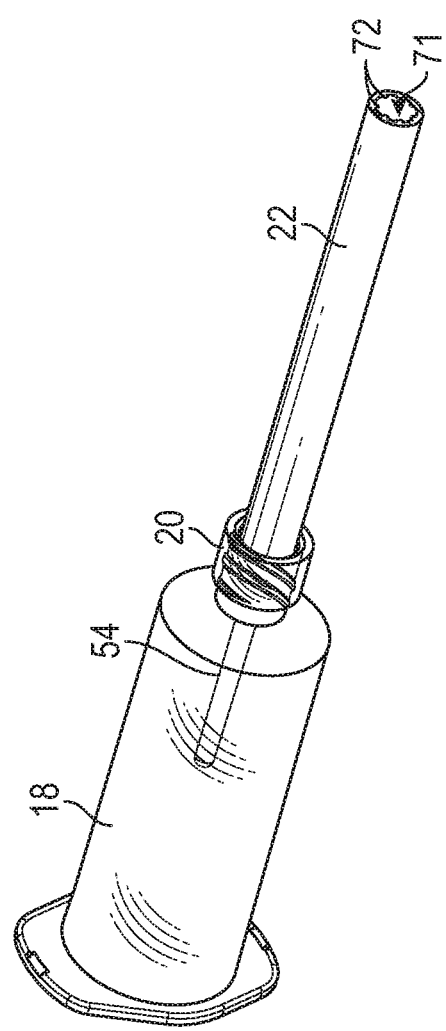
FIG. 5A is another cross-sectional view along the line 1B-1B of FIG. 1A, according to some embodiments.
Figure 5B:
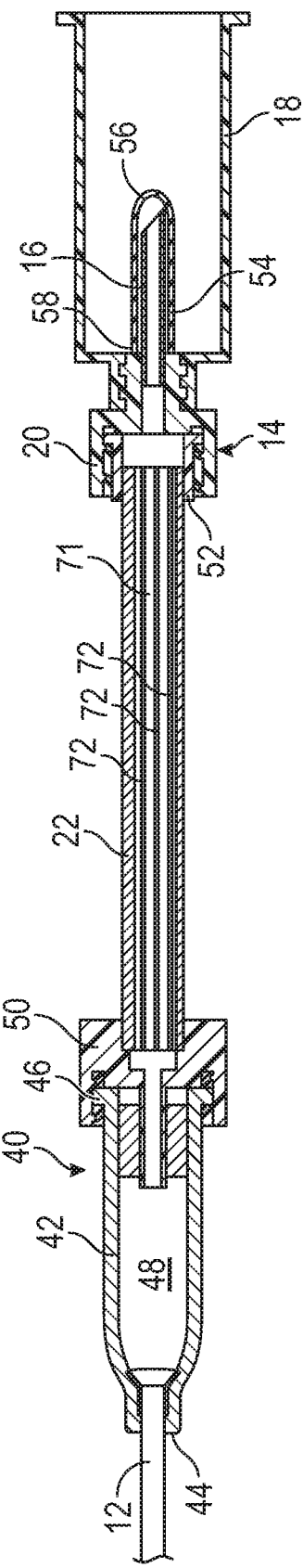
FIG. 5B is another cross-sectional view of the blood collection system of FIG. 1A, according to some embodiments.
Figure 6A:
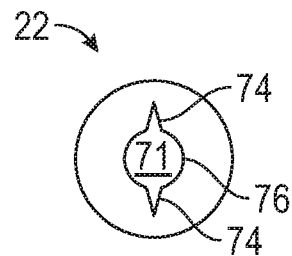
FIG. 6A is a cross-sectional view of another example tubing at a first pressure differential, according to some embodiments.
Figure 6B:
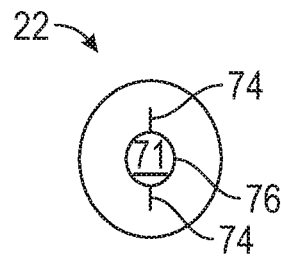
FIG. 6B is a cross-sectional view of the tubing of FIG. 6A at a second pressure differential higher than the first pressure differential, according to some embodiments.
Figure 7A:
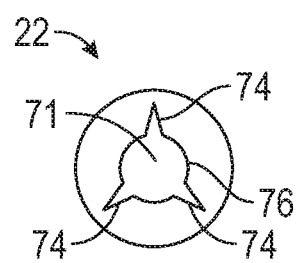
FIG. 7A is a cross-sectional view of another example tubing at a first pressure differential, according to some embodiments.
Figure 7B:
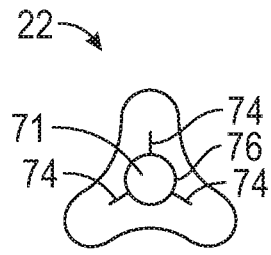
FIG. 7B is a cross-sectional view of the tubing of FIG. 7A at a second pressure differential higher than the first pressure differential, according to some embodiments.
Figure 8A:
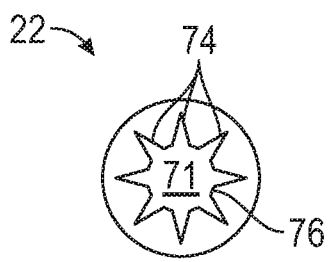
FIG. 8A is a cross-sectional view of another example tubing at a first pressure differential, according to some embodiments.
Figure 8B:
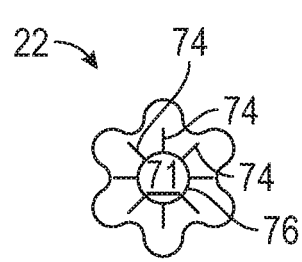
FIG. 8B is a cross-sectional view of the tubing of FIG. 8A at a second pressure differential higher than the first pressure differential, according to some embodiments.

Referring back to FIGS. 5A-5B, in some embodiments, the tubing 22 may include no more than one flow channel 71 extending through the tubing 22. In some embodiments, an inner surface of the tubing 22 may include one or more ribs 72, as illustrated, for example, in FIGS. 5A-5B. In some embodiments, the ribs 72 may extend along a length of the tubing 22 and/or may be generally evenly spaced about a circumference of the inner surface of the tubing 22. In some embodiments, the ribs 72 may maintain a minimum flow rate through the tubing 22 even when the tubing 22 is collapsed. In some embodiments, the outer tubing 62 and/or the inner tubing 64 discussed with respect to FIGS. 3A-4D and 12 may include the ribs 72.

Referring now to FIGS. 6A-8B, in some embodiments, the inner surface of the tubing 22 may include one or more slots 74, as illustrated, for example, in FIGS. 6A-8B. In some embodiments, the tubing 22 may include the one flow channel 71. In some embodiments, the slots 74 may extend along a length of the tubing 22 and/or may be generally evenly spaced about a circumference of the inner surface of the tubing 22. In some embodiments, the inner surface of the tubing 22 may include one slot, two slots, three slots, four slots, or more than four slots, depending on, for example, a desired change in flow rate.

In some embodiments, in response to the spike in the pressure differential, the tubing 22 may collapse such that the slots 74 close, and the flow channel 71 remains open. For example, in response to coupling the evacuated blood collection tube to the blood collection system 10, the tubing 22 may collapse. In some embodiments, the slots 74 may extend outwardly from a generally cylindrical portion 76 of the flow channel 71. In some embodiments, in response to the spike in the pressure differential and the pressure differential reaching the predetermined level, the generally cylindrical portion 76 of the fluid channel may remain open. In some embodiments, in response to the evacuated blood collection tube partially filling with blood, the slots 74 may reopen.

Figure 9A:
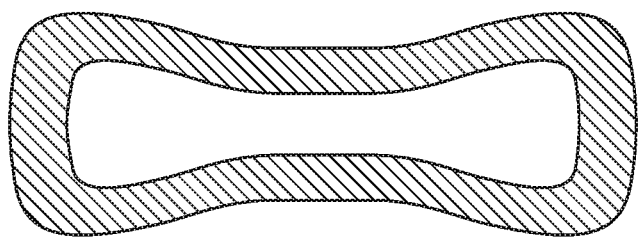
FIG. 9A is a cross-sectional view of another example tubing at a first pressure differential, according to some embodiments.
Figure 9B:
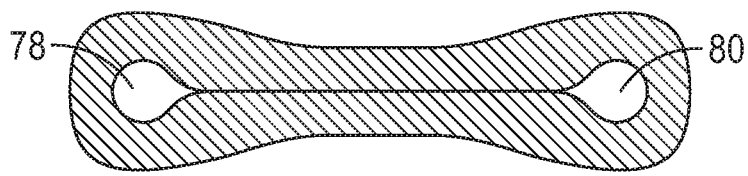
FIG. 9B is a cross-sectional view of the tubing of FIG. 9A at a second pressure differential higher than the first pressure differential, according to some embodiments.

Referring now to FIGS. 9A-9B, the tubing 22 may include a generally hour-glass shape so that its medial portion has a smaller outer diameter and inner diameter than either side. In some embodiments, in response to the spike in the pressure differential and the pressure differential reaching the predetermined level, the tubing 22 may collapse such that the medial portion closes and two flow channels 78, 80 are formed, as illustrated, for example, in FIG. 9B. In some embodiments, in response to the evacuated blood collection tube partially filling with blood, the medial portion may reopen.

Figure 10A:
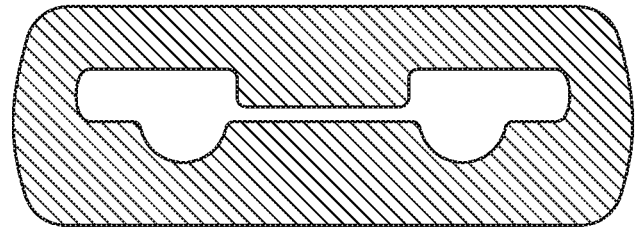
FIG. 10A is a cross-sectional view of another example tubing at a first pressure differential, according to some embodiments.
Figure 10B:
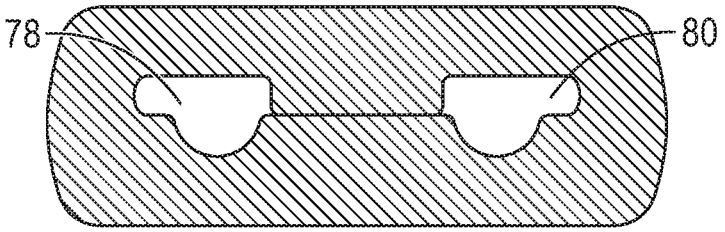
FIG. 10B is a cross-sectional view of the tubing of FIG. 10A at a second pressure differential higher than the first pressure differential, according to some embodiments.

Referring now to FIGS. 10A-10B, a cross-section of an inner lumen of the tubing 22 may include a generally hour-glass shape so that a medial portion of the inner lumen has a smaller diameter than either side of the inner lumen. In some embodiments, in response to the spike in the pressure differential and the pressure differential reaching the predetermined level, the tubing 22 may collapse such that the medial portion closes and one or more flow channels may be formed. For example, in response to the spike in the pressure differential and the pressure differential reaching the predetermined level, the tubing 22 may collapse such that the medial portion closes and the two flow channels 78, 80 are formed, as illustrated, for example, in FIG. 10B. In some embodiments, in response to the evacuated blood collection tube partially filling with blood, the medial portion may reopen.

Figure 11A:
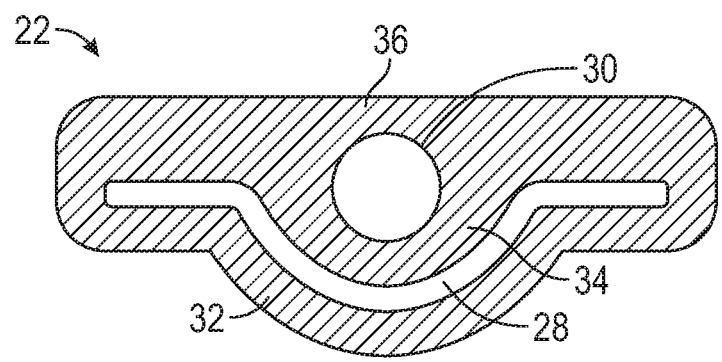
FIG. 11A is a cross-sectional view of another example tubing at a first pressure differential, according to some embodiments.
Figure 11B:
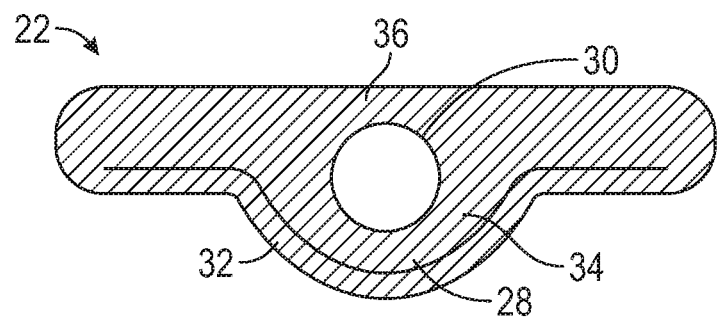
FIG. 11B is a cross-sectional view of the tubing of FIG. 11A at a second pressure differential higher than the first pressure differential, according to some embodiments.

Referring now to FIGS. 11A-11B, the first flow channel 28 and the second flow channel 30 are illustrated, according to some embodiments. In some embodiments, the first flow channel 28 may be configured to collapse at a lower pressure differential than the second flow channel 30. In some embodiments, the first flow channel 28 may collapse in response to the spike in the pressure differential between the evacuated blood collection tube and the vein of the patient. In some embodiments, when the first flow channel 28 collapses, the first flow channel may be partially or completely blocked. In some embodiments, the first flow channel 28 may be elongated and have a narrowed inner diameter along an entirety of its length compared to the second flow channel 30, which may facilitate collapse of the first flow channel 28. In some embodiments, the second flow channel 30 may be generally circular or another suitable shape.

Figure 13A:
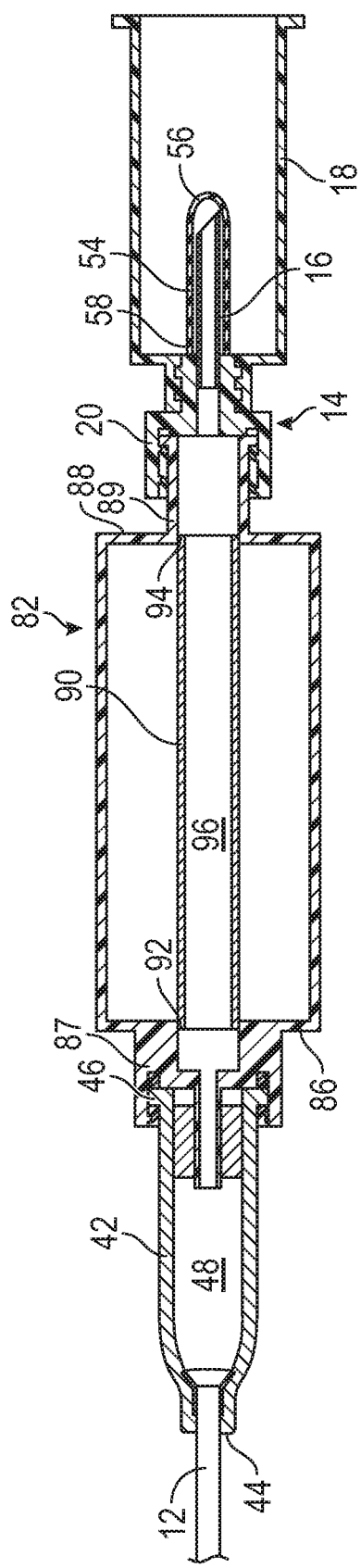
FIG. 13A is a cross-sectional view of another blood collection system, according to some embodiments.
Figure 13B:
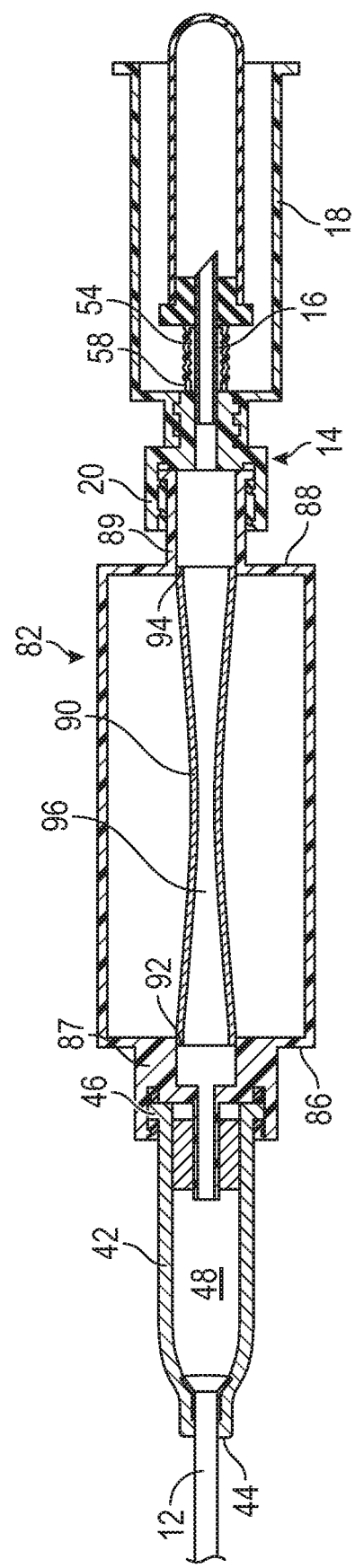
FIG. 13B is another cross-sectional view of the blood collection system of FIG. 13A, illustrating the evacuated blood collection tube coupled to the blood collection system, according to some embodiments.

Referring now to FIGS. 13A-13B, in some embodiments, a blood collection system 82 may include a housing 84. In some embodiments, the blood collection system 82 may be similar or identical to the blood collection system 10 discussed with respect to FIGS. 1A-12D in terms of one or more included features and/or operation. In some embodiments, the housing 84 may include a distal end 86 and a proximal end 88. In some embodiments, the housing 84 may correspond to a tubing. In some embodiments, the distal end 86 may include a luer adapter 87 and/or the proximal end 88 may include a luer adapter 89. In some embodiments, the luer adapter 87 and/or the luer adapter 89 may include a luer lock or luer slip connector. In some embodiments, the luer adapter 87 and/or the luer adapter 89 may include a male or female luer connector. In some embodiments, the proximal end 88 may be integrated with the luer adapter 20 and/or the needle assembly 14.

In some embodiments, the blood collection system 82 may include a tubing 90, which may include a distal end 92 and a proximal end 94. In some embodiments, the tubing 90 may be similar or identical to the tubing 22 discussed with respect to FIGS. 1A-2C and 5A-11B in terms of one or more included features and/or operation. In some embodiments, the distal end 92 and/or the proximal end 94 may be coupled to the housing 84. In some embodiments, the housing 84 may include a higher durometer than the tubing 90. In some embodiments, in response to the spike in the pressure differential and the pressure differential reaching the predetermined level, a flow channel 96 extending through the tubing 90 may collapse, as illustrated, for example, in FIG. 13B. In some embodiments, the flow channel 96 may be closed or restricted in response to the tubing 90 collapsing. In some embodiments, in response to the evacuated blood collection tube partially filling with blood, the flow channel 96 may reopen.

Figure 14:
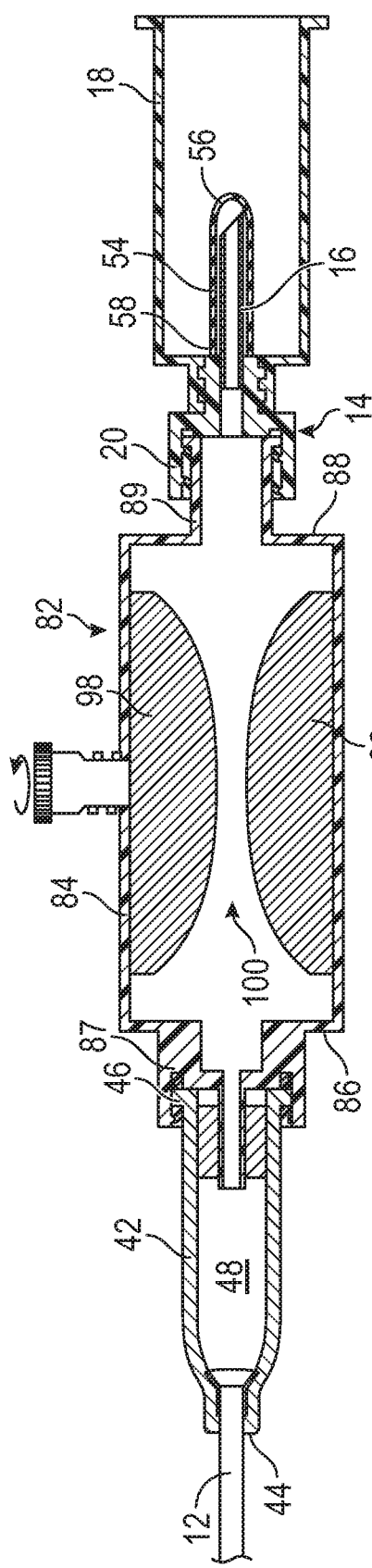
FIG. 14 is a cross-sectional view of the blood collection system of FIG. 13A, according to some embodiments.

Referring now to FIG. 14, in some embodiments, a septum 98 may be disposed within the housing 84. In some embodiments, a flow channel or opening 100 may extend through the septum 98. In some embodiments, the septum 98 may be annular. In some embodiments, a diameter of the opening 100 may be manually adjusted by a user. In some embodiments, the septum 98 may be coupled to a threaded nut, which may be threaded within the housing 84. In some embodiments, the threaded nut may be rotated with respect to the housing 82 to increase or decrease a diameter of the opening 100 extending through the septum 98.

Figure 15A:
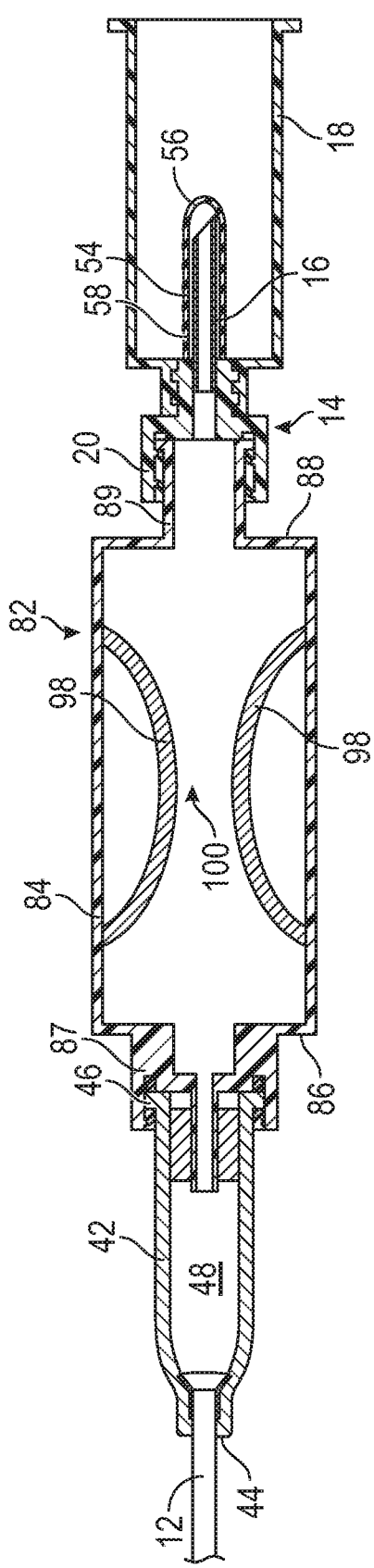
FIG. 15A is a cross-sectional view of the blood collection system of FIG. 13A at a first pressure differential, according to some embodiments.
Figure 16A:
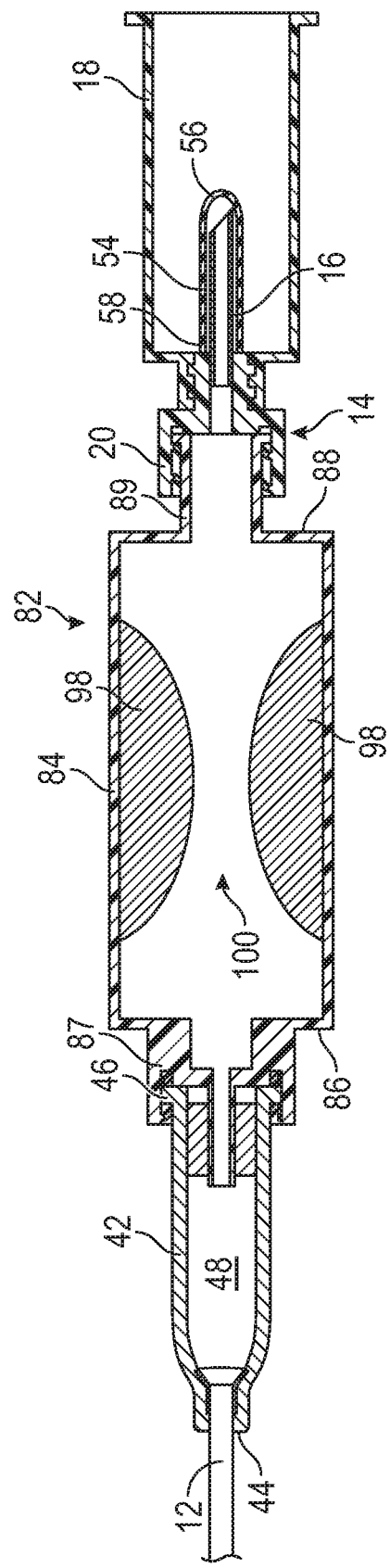
FIG. 16A is a cross-sectional view of the blood collection system of FIG. 13A at a first pressure differential, according to some embodiments.
Figure 15B:
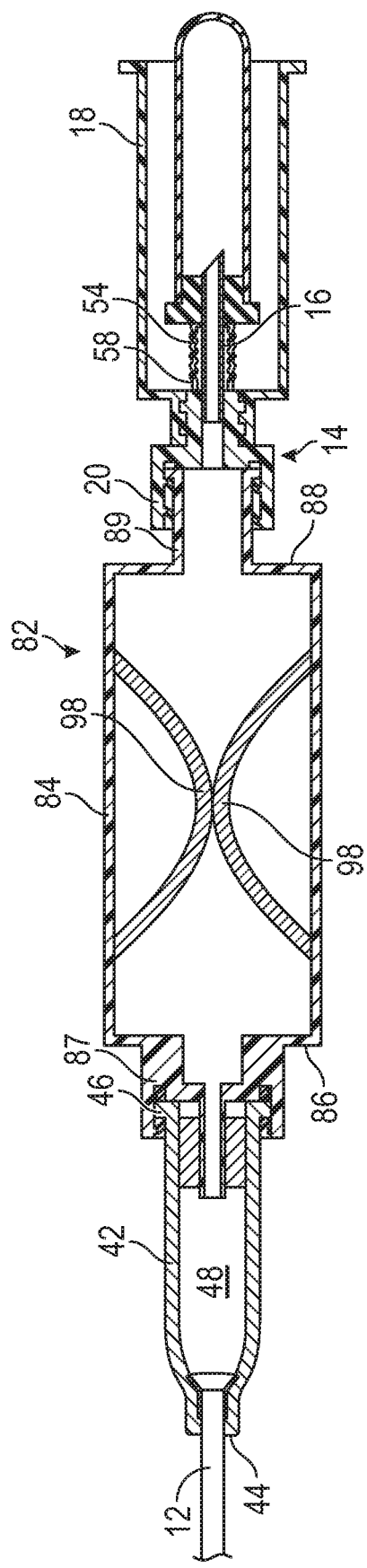
FIG. 15B is a cross-sectional view of the blood collection system of FIG. 15A at a second pressure differential higher than the first pressure differential, according to some embodiments.

Referring now to FIGS. 15A-16B, in some embodiments, the septum 98 within the housing 84 may be partially pressurized with nitrogen or another gas that is compressible. In some embodiments, in response to the spike in the pressure differential, the opening 100 may narrow or close due to presence of nitrogen or the other gas and expansion of the septum 98. In some embodiments, an inner surface of the septum 98 may include two opposing arc-shapes or another suitable shape. As illustrated in FIGS. 15A-15B, in some embodiments, the septum 98 may not contact the housing 84 along an entirety of a length of the septum 98. In some embodiments, the septum 98 may be coupled to the housing 84 at a first point and a second point, and a region between the first point and the second point may be spaced apart from the housing 84. In some embodiments, the region may be arc-shaped or another suitable shape. As illustrated in FIGS. 16A-16B, in some embodiments, the septum 98 may contact the housing 84 along an entirety of a length of the septum 98.

Referring now to FIG. 17, in some embodiments, in some embodiments, the tubing 90 may include a shape that facilitates a Coanda effect. In some embodiments, the tubing 90 may include a first branch 102, which may be generally straight or parallel to a longitudinal axis of the blood collection system 82. In some embodiments, blood within the first branch 102 may be configured to flow in a distal to proximal direction. In some embodiments, a second branch 104 may extend from the first branch 102. In some embodiments, a portion of the second branch 104 proximate the first branch 102 may include a reverse branch, in which blood is configured to flow in a proximal to distal direction. In some embodiments, a distal end of the first branch 102 may extend through the distal end 86 of the housing 84 and/or be coupled with the luer adapter 87. In some embodiments, a proximal end of the first branch 102 and/or a proximal end of the second branch 104 may be coupled to the proximal end 88 of the housing 84 and/or the luer adapter 89.

In some embodiments, in response to a high pressure differential or the spike in the pressure differential, blood traveling through the tubing 90 from the catheter assembly 40 may largely bypass the second branch 104. In some embodiments, in response to the high pressure differential or the spike in the pressure differential, a majority of blood traveling through the tubing 90 from the catheter assembly 40 may largely bypass the second branch 104 and may flow through the first branch 102. In some embodiments, as the pressure differential decreases, more blood may flow through the second branch 104, reducing an overall flow resistance.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

We claim:

1. A blood collection system, comprising:
   a needle assembly, comprising a needle configured to receive an evacuated blood collection tube; and
   a tubing, comprising a distal end and a proximal end, wherein the proximal end is coupled to the needle assembly, wherein the tubing comprises a first flow channel and a second flow channel, wherein the first flow channel is formed by a first wall and a shared wall, wherein the second flow channel is formed by a second wall and the shared wall, wherein the first flow channel is configured to collapse at a lower pressure differential than the second flow channel during blood collection, wherein the collapse of the first flow channel includes caving in of at least one of the first wall and the shared wall to at least partially block the first flow channel,
   wherein the first flow channel is in fluid communication with the second flow channel at the proximal end of the tubing, and wherein the first flow channel is in fluid communication with the second flow channel at the distal end of the tubing.

2. The blood collection system of claim 1, wherein a fluidic resistance of the first flow channel is less than a fluidic resistance of the second flow channel.

3. The blood collection system of claim 2, wherein the first wall comprises a lower durometer than the second wall.

4. The blood collection system of claim 3, wherein the second flow channel comprises a bore hole extending from the distal end of the tubing to the proximal end of the tubing.

5. The blood collection system of claim 1, further comprising a blood collection tube holder coupled to the needle assembly, wherein the blood collection tube holder surrounds the needle.

6. The blood collection system of claim 1, further comprising a catheter assembly, wherein the catheter assembly comprises:
   a catheter adapter, comprising a distal end, a proximal end, and a lumen extending through the distal end of the catheter adapter and the proximal end of the catheter adapter, wherein the distal end of the tubing is coupled to the catheter adapter; and
   a catheter extending distally from the distal end of the catheter adapter.

7. The blood collection system of claim 1, further comprising a male luer adapter coupled to the distal end of the tubing and a female luer adapter coupled to the proximal end of the tubing.

* * * * *